United States Patent [19]
Mazaheri

[11] Patent Number: 6,034,292
[45] Date of Patent: Mar. 7, 2000

[54] EYE CLOSURE APPLIANCE

[76] Inventor: Mehrdad Mazaheri, 435-G Evans St., Williamsville, N.Y. 14221

[21] Appl. No.: 08/604,439

[22] Filed: Feb. 21, 1996

[51] Int. Cl.⁷ .................................................... A61F 13/00
[52] U.S. Cl. ............................................. 602/41; 128/858
[58] Field of Search .................................. 606/213–216; 602/41, 43, 52, 53, 54; 2/15; 128/888, 889

[56] References Cited

U.S. PATENT DOCUMENTS

| | | | |
|---|---|---|---|
| 363,538 | 5/1887 | Penny | 606/215 |
| 4,423,731 | 1/1984 | Roomi | 606/215 X |
| 4,549,539 | 10/1985 | Donaldson | 128/858 |
| 5,144,944 | 9/1992 | Rice | 602/41 X |

FOREIGN PATENT DOCUMENTS

| | | | |
|---|---|---|---|
| 320014 | 4/1920 | Germany | 606/215 |

Primary Examiner—Richard J. Apley
Assistant Examiner—Kim M. Lee

[57] ABSTRACT

Maza-Strips are designed to protect the cornea in patients at high risk for dry cornea and lack of blinking reflex problems. Maza-Strips work by creating a natural closure of the eye lids without the use of any invasive maneuvers. They are used as pairs; one for the upper lid, and one for the lower lid. Each piece is composed of a curvo-linear solid structure material that rests on each lid conforming to the curvature of the lids. Plastic family compounds, metals, or any combination of plastic and metals can be used to make Maza-Strips. Maza-Strips are secured in place with a strong skin adhesive that is coated on the concave side (skin side) of the Maza-Strip. After placing the Maza-Strips on the lids, by using a string or combination of strings that pass though the elevated anchorage loops of Maza-Strips, the two lids are pulled and brought together to close the eye with out getting caught in the lashes or rubbing against the cornea.

19 Claims, 1 Drawing Sheet

EYE CLOSURE APPLIANCE

BACK GROUND

1. Field of Invention

Human cornea is composed of three main layers; the inner endothelial layer, the middle stromal layer, and the external layer (1). The external or the outer layer, which is in contact with air, has to be kept moist at all times (2). Humans blink constantly through out the day to keep the cornea moist, therefor loss of eye lid function can be devastating and ultimately cause loss of vision (3).

The external layers of the cornea which are composed of 5–7 epithelial cell layers, upon dryness and loss of normal blinking reflex, loose their normal form and start separating from the surface. As this process continues the cornea gets eroded and painful. Epithelial defects form on the surface of the cornea and it becomes prone to infection and ulcers (4,5). If not treated promptly this can even ultimately lead to perforation of the cornea. Even though aggressive medical treatment can reverse the process, still corneal scarring and decreased vision can be a the end result.

Patients with sever head injury or loss of innervation to orbicularis muscle are susceptible to corneal related morbidity (2,3,4). Patients on ventilators are also at high risk for corneal problems due to poor eye lid closure (6). Currently, preventive measures include frequent eye ointments and drops to keep the surface of the eye moisten (4,6), however with limited success in patient with long standing loss of blinking reflex and poor eye lid closure. when, conservative therapy fails, a surgical procure known as tarsorrhaphy is performed by some surgeons. In this procedure the eye lids are sutured closed to preserve the cornea (7,8).

The present invention provides a means (referred to as "Maza-Strips" that preserve the cornea from drying damage by keeping the eye closed without the need for a surgical procedure. Maza-Strips are as effective as suturing the eyes closed, because they also induce the same physiologic function, however they are non surgical and do not involve any invasive maneuvers. They also have the advantage of allowing to open the eyes by simply removing the strings and later putting them back on. This is important for checking the pupils in a patient that might need frequent pupillary exams secondary to head trauma (9).

2. Description of Prior Acts

Rice has patented (U.S. Pat. No. 5,144,944) an eye pad dressing for the upper lids. This patent claims that it is a multi layer pad that is thin and narrow enough to NOT cause occlusion of the eye. This exactly is the opposite function of the maza-strips. Also, because it is in essence a dressing pad to stop the bleeding, it does not have a solid curvo-linear structure, or the anchorage loops. It was meant for a very different function.

Penned patent # 363538 is used for closing flesh wounds and ulcers, therefore they do not have a solid curvo-linear structure. Structural component of maza-strips also at the time of string stress lift the upper lid and bring it downward, this is better than a strait pulling mechanism that might elevate the intraocular pressure; which is very important in the settings of an eye with already high pressures. Penned pads are narrow in the axis of the strain to which they will be subjected, and this is also different from maza-strips.

Roomi patent U.S. Pat. No. 4,423,731 and the German patent # 320014 are both strips made for closing a wound gap. They were not designed in a solid curvo-linear manner with elevated anchorages on the convex surface to fit and close the eye lids. The anchorage elevation from the convex surface also serves to keep the suture strings in the air away from the lashes to avoid disrupting and entangling the eye lashes.

SUMMARY OF INVENTION

The eye closure appliances according to the present invention ("Maza-Strips") are designed to protect the cornea in patients at high risk for corneal dryness and lack of blinking related problems. Maza-Strips work by creating a natural closure of the eye lids without the use of any invasive maneuvers. Currently, there are no practical and cost efficient ways to save the eyes that lack lid function. Most hospitals put expensive ointments around the clock in these eyes to keep it moist, however it is not only very difficult for the nurses, it is also not successful in many cases. Many patient get ulcers that require long term treatment and compromised vision or loss of the eye, inadition to the cost of multiple visits or consults from the eye surgeons. Some of these patients after recovery from the hospital end up having corneal transplants or permanent surgical closure of the eye lids.

When the human eye is kept open for more than a few minutes, that is if the blinking is stopped, the corneal epithelium will start to separate and brake down. This is the initial process to corneal ulcers, and it is very common in all comatose patient; patients after lid surgery, stroke, severed facial nerve, bells palsy, senile loss of eye lid structure, Parkinson' disease, and corneal de-innervation are just a few more groups that are at high risk for corneal problems.

Maza-Strips are used as pairs; one for the upper lid, and one for the lower lid (FIGS. 1,2,3,4). Each piece is composed of a material that rests on each lid conforming to the curvature of the lids. Plastic family compounds, metals, or any combination of plastic and metals can be used to make Maza-Strips.

Maza-Strips are secured in place with a strong skin adhesive that is coated in the concave side of the Maza-Strip. On the convex side it has two or more anchorage loops as seen in FIGS. 1&2.

After placing the Maza-Strips on the lids, by using a string or combination of strings or rubber band that courses through the anchorage loops, the two lids are pulled together, in order to close the eye lids as demonstrated in FIGS. 3&4.

The two lids are brought together by different mechanisms.

1) The pulling force created by a string or rubber band between the opposite Maza-Strips.

2) The upper lid because of the lid expansion caused by the width of the Maza-Strip, when placed on the upper lid, is placed downward.

3) The lower lid has less motion, so, when the string or rubber banned is placed, the vector force will exert some force away from the globe anteriorly. This will slightly lift the upper lid from the cornea to enhance a better closure and less strain on the globe.

DESCRIPTION OF THE PREFERRED EMBODIMENT

Figure 1:
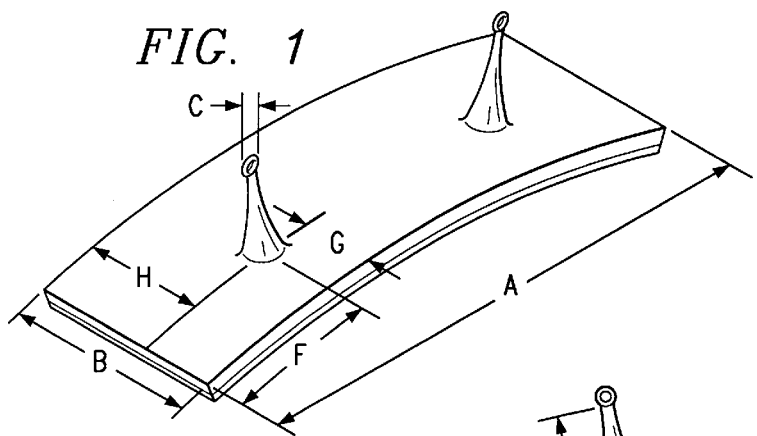
FIG. 1 is a top view of the Maza-strips, over looking the convex surface.
Figure 2:
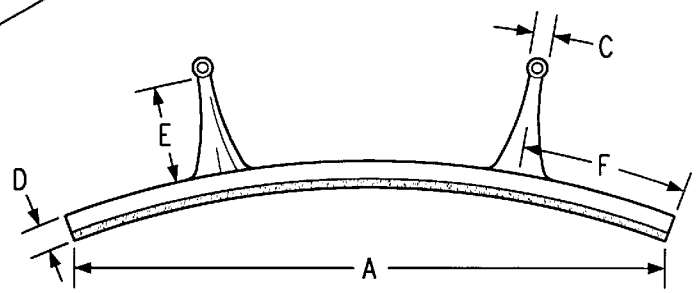
FIG. 2 is an anterior cross sectional view of the Maza-strips.
Figure 3:
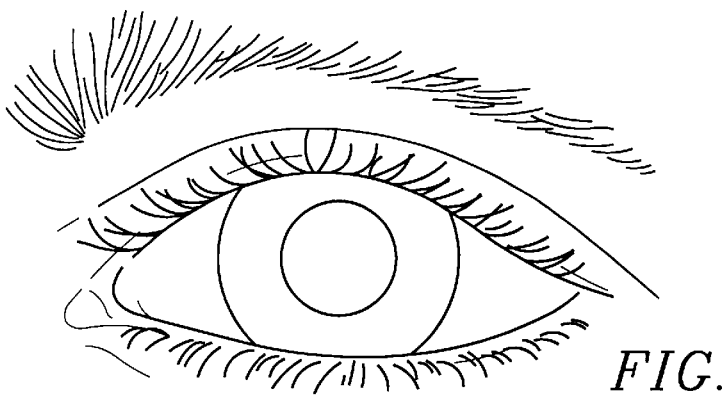
FIG. 3 is a frontal view of an open eye.
Figure 4:
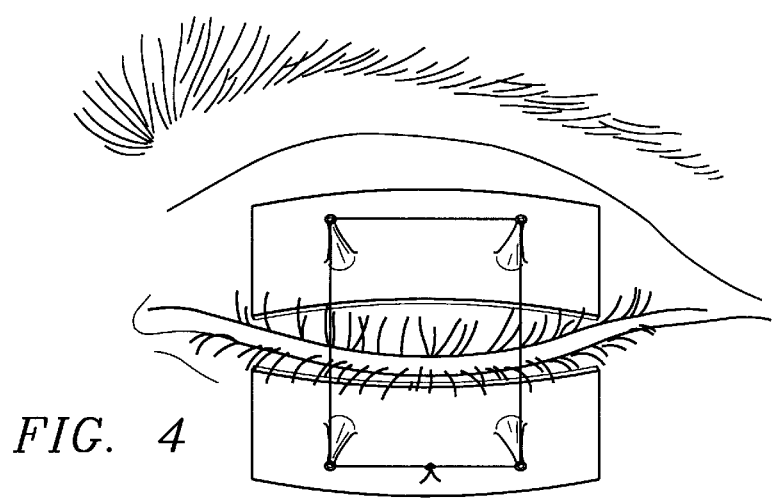
FIG. 4 is a frontal view of a closed eye after closure with Maza-strips.

The present invention provides an eye closure device. The eye closure device or appliance according to the present invention (referred to hereafter as "Maza-Strip" or "Maza-Strips") are used as pairs. They are secured on the lids with strong adhesive coating on the concave surface. Then, by using a string through the anchorage loops, the eye lids are pulled in to closure (FIGS. 3&4).

A: represents the horizontal length when placed over the eye (22 millimeters, mm). B: represents the width, this would be the distance between the eye lash side of the lid towards the origin of the lid the when the strip is placed over the eye (8 mm). C: represents the ring or the anchorage site that is elevated from the surface (4 mm in diameter). D: represents the thickness of the strip (2 mm). E: Represents the anchorage elevation (3 mm). G,F&H: represent the distance of the anchorage site on the convex surface that are 4 mm away from each edge of the mala-strip.

Having thus describe my invention, following claims are made:

1. An eye-closure appliance comprising:
   a pair of curved rigid members adapted to rest on a patient's upper and lower eyelids, respectively, the rigid members having a concave side which contours the shape of the eyeball and a convex side, the concave side applied to the eyelids of the patient during use;
   means for securing the rigid members to the eyelid; and
   coupling means for securing the pair of curved rigid members together so as to draw the upper and lower eyelids closed.

2. The eye-closure appliance according to claim 1, wherein the rigid member is a rectangular, plastic strip.

3. The eye-closure appliance according to claim 1, wherein the aperture is formed in a portion of the rigid member standing perpendicular to the convex side of the rigid member.

4. The eye-closure appliance according to claim 3, wherein the portion of the rigid member standing perpendicular to the convex side of the rigid member is a ring.

5. The eye-closure appliance according to claim 3, wherein the portion of the rigid member standing perpendicular to the convex side of the rigid member is a hook.

6. The eye-closure appliance according to claim 1, wherein the securing means comprises at least one aperture extending through the rigid member from the convex to the concave side for passage of superficial sutures through the eyelid to secure the rigid member thereto.

7. The eye-closure appliance according to claim 1, wherein the securing means comprises an adhesive on at least the concave side of the rigid member for adhering the strip to the eyelid.

8. An eye-closure appliance, the appliance comprising.
   a pair of rigid members, each of the rigid members having a curvature defining a concave surface and a convex surface, the concave surface adapted to rest on a patient's eyelid and conform to the curvature of the eyelid;
   means for securing each of the rigid members to the patient's eyelid; and
   coupling means for securing one of the pair of rigid members to another of the pair of rigid members.

9. The eye-closure appliance according to claim 8, wherein each rigid member is a rectangular, plastic strip.

10. The eye-closure appliance according to claim 8, wherein the coupling means comprises:
    at least one aperture formed in a portion of each rigid member standing perpendicular to the convex side of the rigid member; and
    an elastic member secured at each end to the aperture of each of the pair of rigid members and extending therebetween to maintain the patient's eyelid in a selected position.

11. The eye-closure appliance according to claim 10, wherein the portion of the rigid member standing perpendicular to the convex side of the rigid member is a ring.

12. The eye-closure appliance according to claim 10, wherein the portion of the rigid member standing perpendicular to the convex side of the rigid member is a hook.

13. The eye-closure appliance according to claim 8, wherein the securing means comprises at least one aperture extending through the rigid member from the convex to the concave side for passage of superficial sutures through the eyelid to secure the rigid member thereto.

14. The eye-closure appliance according to claim 8, wherein the securing means comprises an adhesive on at least the concave side of the each of the rigid members for adhering the strip to the eyelid.

15. The eye-closure appliance according to claim 8, wherein the coupling means comprises:
    at least one aperture formed in a portion of each rigid member standing perpendicular to the convex side of the rigid member; and
    an inelastic member extending between each of the pair of rigid members.

16. An eye-closure appliance, the appliance comprising:
    a pair of rigid curved strips, each strip being generally rectangular and defining a concave side conforming to a curvature of an eyelid of a patient and a convex side opposite the concave side;
    an adhesive on the concave side of each strip for securing the strip to the eyelid;
    at least one partially circular ring secured to and standing perpendicular to the convex side; and
    coupling means for securing the strips together.

17. The eye-closure appliance according to claim 16 further comprising:
    at least on aperture formed through each strip, through which sutures may be passed to secure the strip to the eyelid.

18. The eye-closure appliance according to claim 16, wherein each circular ring is located on the strip for closing a sectoral portion of the eyelid.

19. The eye-closure appliance according to claim 16 wherein the circular rings are open to define a hook.

* * * * *